(12) United States Patent
Keays

(10) Patent No.: US 8,707,758 B2
(45) Date of Patent: *Apr. 29, 2014

(54) SOBRIETY MONITORING SYSTEM

(75) Inventor: Brad Keays, Manhattan Beach, CA (US)

(73) Assignee: Soberlink, Inc., Cypress, CA (US)

( * ) Notice: Subject to any disclaimer, the term of this patent is extended or adjusted under 35 U.S.C. 154(b) by 125 days.

This patent is subject to a terminal disclaimer.

(21) Appl. No.: 13/357,494

(22) Filed: Jan. 24, 2012

(65) Prior Publication Data

US 2013/0021153 A1    Jan. 24, 2013

Related U.S. Application Data

(63) Continuation-in-part of application No. 13/274,553, filed on Oct. 17, 2011, which is a continuation-in-part of application No. 12/882,323, filed on Sep. 15, 2010, now Pat. No. 8,381,573.

(60) Provisional application No. 61/320,168, filed on Apr. 1, 2010, provisional application No. 61/254,575, filed on Oct. 23, 2009, provisional application No. 61/248,364, filed on Oct. 2, 2009.

(51) Int. Cl.
*G01N 33/497* (2006.01)

(52) U.S. Cl.
USPC .............................. 73/23.3; 422/84

(58) Field of Classification Search
USPC .............................. 73/23.3; 422/84
See application file for complete search history.

(56) References Cited

U.S. PATENT DOCUMENTS

| | | |
|---|---|---|
| 6,726,636 B2 | 4/2004 | Der Ghazarian et al. |
| 6,748,792 B1 | 6/2004 | Freund |
| 7,341,693 B2 | 3/2008 | Der Ghazarian et al. |
| 7,462,149 B2 | 12/2008 | Hawthorne et al. |
| 7,611,461 B2 | 11/2009 | Hawthorne et al. |
| 7,636,047 B1 | 12/2009 | Sempek |
| 7,641,611 B2 | 1/2010 | Hawthorne et al. |
| 7,934,577 B2 | 5/2011 | Walter et al. |

(Continued)

FOREIGN PATENT DOCUMENTS

WO    WO 2008/076310    6/2008

OTHER PUBLICATIONS

"Hand-held Analytical Power for Workplace Monitoring," News Release from Quantitech Ltd, Jul. 2, 2004. Accessed online on Jul. 29, 2013 at <http://www.edie.net/news/0/Hand-held-Analytical-Power-for-Workplace-Monitoring/8540/>.*

(Continued)

*Primary Examiner* — Lisa Caputo
*Assistant Examiner* — Punam Roy
(74) *Attorney, Agent, or Firm* — One LLP

(57) ABSTRACT

A system and method of monitoring sobriety using a handheld breath testing device that, on receipt of a user's breath, generates a breath test signal comprising substance content data and user identification data, and wirelessly transmits the breath test signal to a breath test signal receiving station. The breath test signal includes substance content data and user identification data. The substance content data includes at least one of: a blood alcohol level and a narcotics presence. The user identification data includes compressed image data. The signal receiving station is monitored by a supervisor who is able to intervene should the substance level be greater than a predetermined threshold, or should the user identification data no match with a reference user identification data.

8 Claims, 10 Drawing Sheets

(56) References Cited

U.S. PATENT DOCUMENTS

| | | |
|---|---|---|
| 8,249,311 B2 | 8/2012 | Endo et al. |
| 2002/0127145 A1 | 9/2002 | Der Ghazarian et al. |
| 2006/0202838 A1 | 9/2006 | Hawthorne et al. |
| 2007/0144812 A1 | 6/2007 | Stewart |
| 2007/0239992 A1 | 10/2007 | White et al. |
| 2007/0258894 A1* | 11/2007 | Melker et al. ............ 424/9.1 |
| 2008/0009693 A1 | 1/2008 | Hawthorne et al. |
| 2008/0183502 A1 | 7/2008 | Dicks et al. |
| 2009/0182216 A1 | 7/2009 | Roushey, III et al. |
| 2009/0201138 A1 | 8/2009 | Ghazarian et al. |
| 2009/0293589 A1 | 12/2009 | Freund |

OTHER PUBLICATIONS

Manolis, A., "The Diagnostic Potential of Breath Analysis," Clin. Chem. 29/1, pp. 5-15 (1983).*

Ahlber, P. "Electronic Nose Offers Food Processors a Powerful New Smell Identification Tool," Food Online. Mar. 13, 2000. Accessed online <http://www.foodonline.com> on Jul. 29, 2013.*

Millward, D., "Motorists face roadsied drug tests under government plans," Telegraph. May 10, 2009.*

Millward, D., "Roadside drug testing device developed by academics," Telegraph. Nov. 15, 2011.*

International Search Report, PCT/US2010/050930, Apr. 3, 2012.

http://www.elmotech.com/uploaded/Mems-ewb.pdf, Aug. 12, 2010.

http://www.web.archive.org/web/20090311081549/ http://alcoholmonitoring.com/index/scram/what-is-scram, 2008.

http://www.intoxalock.com/intoxalock-alcohol-monnitoring-systems.cfm, Oct. 15, 2012.

USPTO Form 892—List of References in connection with U.S. Appl. No. 12/882,323, dated Jan. 15, 2013.

USPTO Form 892—List of References in connection with U.S. Appl. No. 12/882,323, dated Sep. 11, 2012.

Gary Mullett, Wireless Telecommunications Systems and Networks (Thomson 2006).

Draft inter partes request for review re: related U.S. Pat. No. 8,381,573, 2013.

* cited by examiner

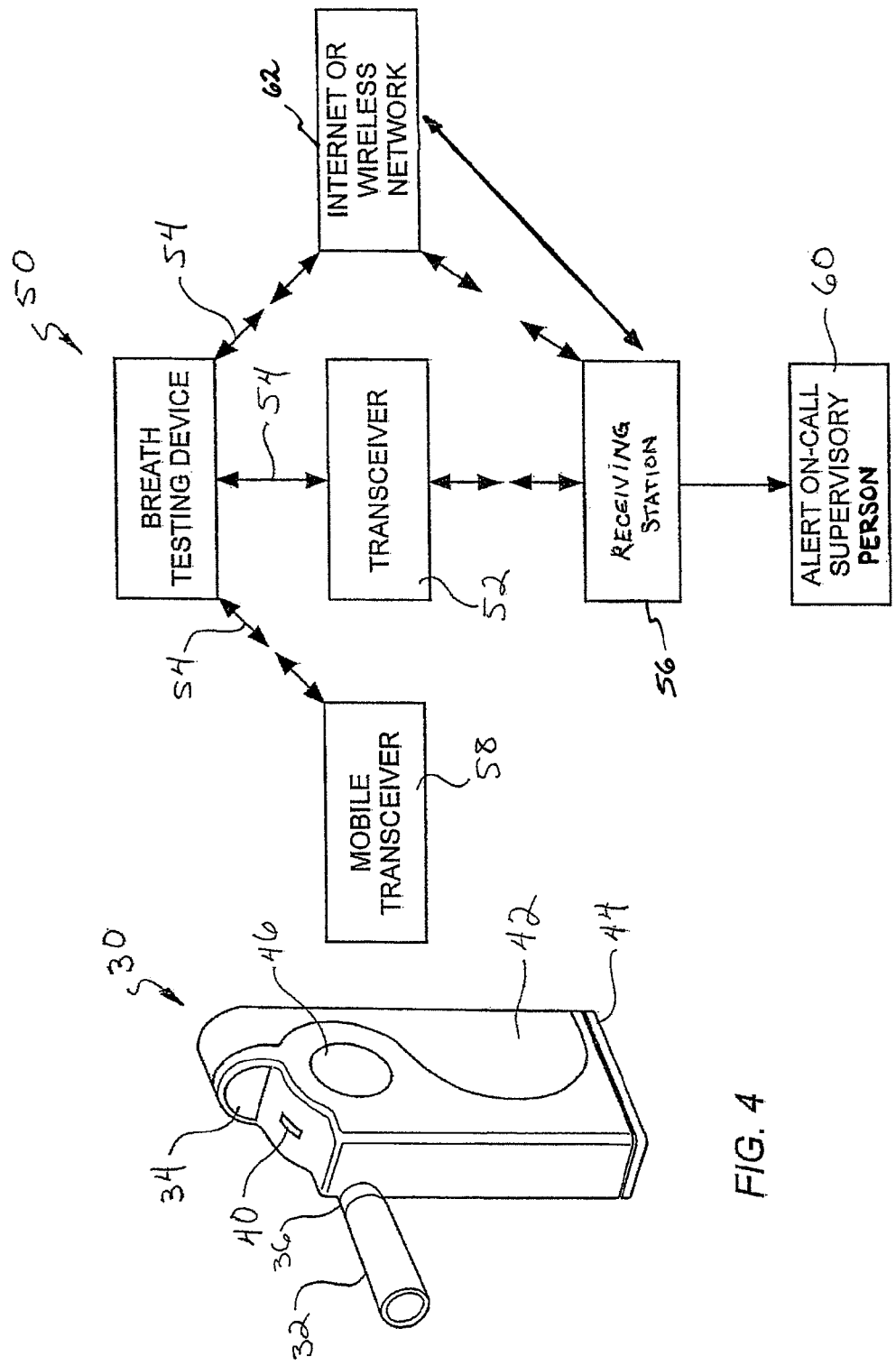

SOBRIETY MONITORING SYSTEM

CROSS-REFERENCE TO RELATED APPLICATIONS

This application is a continuation-in-part application of U.S. Ser. No. 13/274,553, filed Oct. 17, 2011, which is a continuation-in-part application of U.S. Ser. No. 12/882,323, filed Sep. 15, 2010, now U.S. Pat. No. 8,381,573 which is based on U.S. Provisional Application No. 61/320,168, filed Apr. 1, 2010; U.S. Provisional Application No. 61/254,575, filed Oct. 23, 2009; and U.S. Provisional Application No. 61/248,364, filed Oct. 2, 2009, the contents and disclosures of which are herein incorporated by reference.

BACKGROUND OF THE INVENTION

Field of the Present Disclosure

This disclosure relates generally to a method and system for remote sobriety monitoring, and more particularly relates to a method and system utilizing a breath testing and identification device for periodically analyzing the alcohol content or other substance content of the breath of a user in combination with a wireless or cellular transmitter or transceiver device to transmit an alcohol content or other substance content signal to a wireless or cellular signal receiver and/or monitoring station to help ensure abstinence of the user from the use of alcohol or another substance.

Recovering alcoholics or other substance abusers may benefit from the supervision of a sober chaperone such as a sober buddy, sober companion or sober coach to assist a recovering alcoholic in maintaining abstinence from alcohol outside of a treatment facility. Such a sober companion commonly chaperones the recovering alcoholic or substance abuser on a constant basis, or maybe available on an on-call basis to accompany a recovering alcoholic or substance abuser periodically or as needed during certain activities. Such supervisory care can be quite expensive, which may have the unfortunate consequence of reducing or eliminating the services of such supervisory care.

People struggling with alcohol often conceal their abuse, making it difficult for concerned family members to confirm their suspicions and intervene. Because alcohol leaves the system quickly, it is important to test for alcohol consumption by using a breathalyzer or another similar alcohol testing method. Confirmation of a drinking problem becomes increasingly difficult during periods when testing for alcohol consumption is not easily enforced, such as during travel for business or college, for example. It would be useful to provide a method for parents to be able to monitor alcohol use anywhere by their children, and for spouses to monitor alcohol use anywhere by their spouses, in order to eliminate suspicions and confirm whether the family member has a drinking problem. It would also be useful to provide a method for companies to deter alcohol abuse by employees during work hours. Industries that rely heavily on driving and have limited employee supervision could also benefit from a method allowing the monitoring of alcohol use by employees as a way to confirm employee sobriety during work hours. Although drug testing is common in the workplace, since alcohol is metabolized relatively quickly, and is not easily tested, it would also be useful to provide a method for immediate confirmation of an employee's alcohol level at any given time.

Additionally, alcohol and drug abuse sometimes occur together, and the struggles facing recovering alcoholics often mirror those facing recovering drug addicts. Those struggling with narcotics also often conceal it from friends and family, often prolonging intervention until it is too late. Drug abuse is especially prevalent with teenagers. Because of the potentially dangerous side effects of narcotic use, it is important to test for use of narcotics or other controlled substances in a manner that is quick and reliable. It is furthermore important that timely responsive action be taken to prevent injury, disease or death. Furthermore, although drug testing is common in the workplace, current testing methods do not provide immediate confirmation of an employee's sobriety. It would therefore be useful to provide a method for quick and accurate on-demand drug testing and monitoring that can be accomplished with relative ease and convenience.

Court ordered sobriety is also commonly required as a condition of probation or other court imposed rehabilitative or behavior altering programs. Reporting to a stationary facility, one's probation officer, or even one's home in order to be tested for substance use is often an embarrassing and time consuming ordeal that does not facilitate healthy reintegration into society. Thus, the discrete remote monitoring of a person under such a program by the court, or other authority, without requiring the monitored person to excuse themselves from society for more than a brief period of time would be useful in reintegrating the monitored person into society without the awkward and embarrassing effects of traditional monitoring procedures. Such a system is also useful to provide a system of monitoring where those monitored are emboldened to no longer feel like societal outcasts and are thus increasingly motivated to maintain their sobriety.

Currently available remote sobriety monitors involve an intrusive and awkward looking bracelet that requires constant contact with a user's skin. For example U.S. Pat. No. 7,641,611, to Hawthore, et. al., describes an example of one such a remote sobriety monitor requiring the use of skin contacting bracelet. While such monitors enable remote monitoring of blood alcohol levels, users are often stigmatized by their indiscrete presence and therefore find healthy societal interaction while wearing such bracelets difficult.

Non-skin-contact sobriety monitors are available, but they are generally bulky, expensive, inconvenient systems that require a user to periodically return to the sobriety monitor site. For example, the ElmoTech MEMS 3000 system provides a breathalyzer-type sobriety monitor with user image confirmation and remote transmission capabilities. However, the ElmoTech MEMS 3000 sobriety monitor is incapable of being easily transported with the user. Since the user must periodically return to the sobriety monitor site, the user's mobility is extremely limited.

Hand-held breathalyzer-type sobriety monitors such as the monitors in U.S. Pat. No. 6,726,636, to Der Ghazarian et al., are preferable, however because of physical size limitations such hand-held systems do not contain the ability to capture and quickly transmit the user's image for positive identification. Furthermore such hand-held monitors do not transmit complex blood alcohol levels, and instead transmit only simple "pass" or "fail" signals. Thus, recipients of the signals are generally unaware of the user's actual test results. Also, these systems generally are not enabled to provide a vehicle interlock function whereby the breathalyzer is enabled to selectively prohibit vehicle ignition.

There are existing vehicle interlock devices, whereby a breathalyzer is required to enable a vehicle to function; however, such interlock devices are not portable, and further, existing interlock devices can be easily hacked and/or tampered with. For example, a drunk driver can simply have a sober person blow into the breathalyzer to enable vehicle ignition.

It would therefore be desirable to provide a method and system of providing supervisory monitoring of sobriety that is discrete, portable, tamper-proof, and effective, and that can automatically alert a monitoring station of the need for attention and possible corrective or medical action by such a supervisory sober buddy or sober companion on an on-call basis. The present invention meets these and other needs.

BRIEF SUMMARY OF THE INVENTION

Briefly, and in general terms, the present invention provides for a method and system for monitoring sobriety of a user on an automated basis, utilizing a hand-held breath testing device, a wireless or cellular transmitter or transceiver device for wirelessly transmitting results of the breath testing to a wireless or cellular receiver monitoring station. The monitoring station receives the breath testing results (and optionally identification such as a photograph) from the wireless or cellular transmitter or transceiver device, and indicates an alarm or otherwise alerts an on-call monitor when the wireless or cellular transmitter or transceiver is indicated to be off, or when the breath testing results indicate a breath test content greater than a predetermined threshold, or when the received breath is not the breath of the user (which can be determined from the photograph). The method and system can be used in connection with a traditional sober buddy, chaperone service on an on-call basis only, to limit the expense and labor intensiveness of the supervisory care. Such a systems may also be used to monitor abstinence from other drugs which can be taken orally and tested by breath analyzer or the like without the use of a chaperone on a continuing basis.

By using the method and system of the present invention, a family member trying to build back trust in family relationships can prove that they are making behavior changes by sending breath test reports on a predetermined schedule, or when randomly requested by the family. The present invention helps a person prove that they are making healthier choices in life and making steps toward rebuilding trust in family relationships. Families can benefit from knowing that loved ones are sober enough to drive, and the present invention can be used remotely to determine a person's sobriety or that blood alcohol levels are in an acceptable range.

The present invention also provides a method for immediate confirmation of an employee's alcohol level at any given time. Particularly those companies with employees who drive as a part of their employment would benefit by keeping their employees sober during working hours. The present invention also can be used in rehabilitative aftercare, and can be used to monitor multiple patients, and the present invention can be used by a sober companion during times when they were not able to accompany them.

The present invention is also useful for remotely monitoring sobriety in situations in which sobriety has been required as a condition of probation or by courts. In addition, counties and states who sentence an individual to home detention always require sobriety. By incorporating a GPS tracking module or using the mobile device GPS in the breath testing and identification device, the sobriety and location of individuals placed under home detention can be monitored together, which could eliminate the need for the use of ankle bracelets that are currently in use for home detention.

For families who want to monitor their children or spouses, the sobriety monitoring system of the present invention can send a breath test report and photograph to a monitoring station where the report and photograph can be stored, or can send a breath test report and photograph directly from one mobile device to another, without storage of the report and photograph. A cellular module can alternatively be provided inside the breath testing and identification device that can send a breath test report and photograph directly through WiFi, cell towers, or through other mobile wireless networks such as those that do not rely on fixed infrastructure, for example.

These and other aspects and advantages of the invention will be apparent from the following detailed description and the accompanying drawing, which illustrates by way of example the features of the invention.

BRIEF DESCRIPTION OF THE SEVERAL VIEWS OF THE DRAWING(S)

Illustrated in the accompanying drawing(s) is at least one of the best mode embodiments of the present invention In such drawing(s):

FIG. 4 is a left front perspective of the breath testing and identification device of FIG. 3.

FIG. 5 is a schematic diagram illustrating another embodiment of the method and system for monitoring sobriety, according to the invention.

DETAILED DESCRIPTION OF THE INVENTION

The above described drawing figures illustrate the described apparatus and its method of use in at least one of its preferred, best mode embodiment, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present apparatus and its method of use.

Described now in detail is a method and system for monitoring sobriety of a user, such as a recovering alcoholic, as an intermediate, automated way of engaging the services of a sober buddy, sober companion, sober coach, or other supervisory care for the user to help ensure against relapse of the user, and to help the user maintain sufficient abstinence from alcohol or another substance to reside and function outside of a treatment facility.

Figure 1:
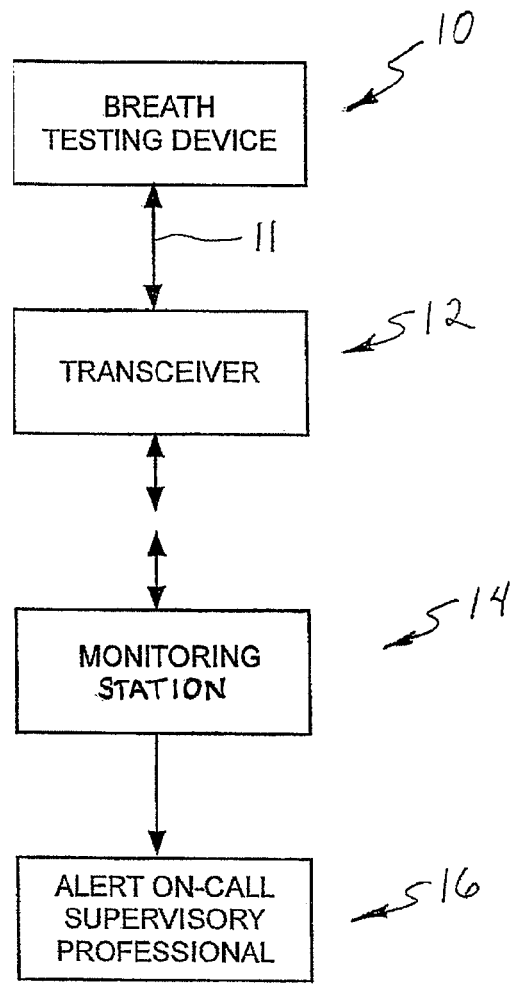
FIG. 1 is a schematic diagram illustrating the method and system for monitoring sobriety, according to the invention.

Referring to FIG. 1, a substance testing device 10; a transceiver unit 12; a receiving station 14; and a supervisory monitor 16 may be provided.

Preferably, the substance testing device 10 is a hand held substance testing device operable to test for the presence of alcohol or other substance in the breath of the user. The testing device may also operate to test the quantity of alcohol or other substance in the breath of the user. Additionally, the substance testing device 10 is preferably operable to generate a substance content signal 11 comprising at least substance content data. For example, the testing device may comprise a breathalyzer type testing device operable to analyze the alcohol content of the breath of a user and generate an alcohol content signal indicative of the alcohol content of the user's breath.

In some embodiments, the substance testing device may also comprise a user identification device (UID) 24, described in detail below, operable to generate a user identification data. For example, the UID may comprise a camera operable to generate a JPEG image of the user while the test is in progress. Thus, the substance content signal 11 may also comprise a user identification data.

Additionally, in some embodiments, the substance testing device may also comprise a GPS module, described in detail below, operable to generate a location data. Thus, the substance content signal 11 may also comprise a location data.

As described in depth below, the transceiver unit 12 may be a wireless or cellular transmitter or transceiver device. It may be a smart cellular phone such as an iPhone that may be configured to be connected to the breath testing device either directly, such as by electrical connection, or wirelessly, so as to receive the content signal 11. Additionally, the transceiver unit 12 may be configured to transmit the content signal 11 to the receiving station 14. Transmission may occur over a wireless, wired, cellular, or any other type of network now known or hereafter developed. In at least one embodiment, the transceiver unit 12 is internal to the substance testing device 10 and is a hardware component thereof.

The receiving station 14 may be configured to receive the content signal 11. The receiving station 14 may be configured to inform the supervisory monitor 16 if the content signal 11 is not received from the transceiver at a predetermined time, or if the content signal 11 indicates that the substance content levels exceed a predetermined threshold. For example, the typical legal limit of blood alcohol content (BAC) is 0.08%. Thus, receiving station may inform the supervisory monitor 16 if the content signal indicates the user's BAC is greater than 0.08%. Importantly, the predetermined threshold may be set at a higher or lower level as may be desired. Additionally, the receiving station 14 may be configured to convey the content signal 11, or a report based thereon, directly to the supervisory monitor 16 so that the supervisory monitor 16 is made aware of the substance content data. Thus, for example, the receiving station may inform the supervisory monitor 16 (who may be a parent or guardian) that the user (who may be a teenage child of the parent or guardian) has a BAC of 0.03%.

In some embodiments, the receiving station 14 may comprise any location, device or system where the content signal 11 is received, including, for example: a monitoring station, a cellular/smart phone, an email account, a website, a network database, and a memory device. Additionally, the supervisory monitor 16 may comprise a parent, guardian, family member, friend, parole officer, court appointed supervisor, sobriety coach, sober buddy, sober companion, police department, or other supervisory care person, group, or authority.

In some embodiments, the substance testing device 10 is a breathalyzer type device, such as the iBreath Breathalyzer, usable in combination with an iPod or iPhone, for example, which may act as a power source for the iBreath.

Figure 8:
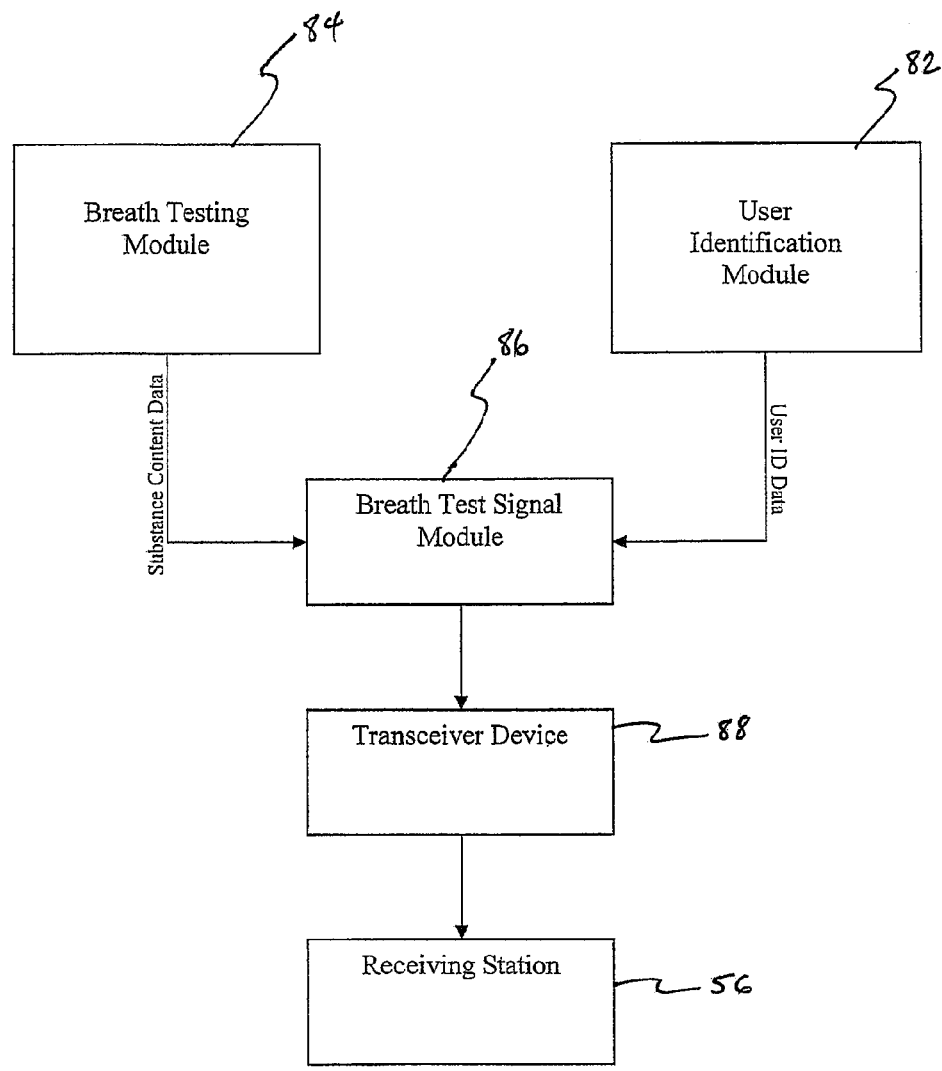
FIG. 8 is a schematic diagram illustrating another the method and system for monitoring sobriety, according to a preferred embodiment of the invention.

According to at least one embodiment, there may be provided a user identification module 82 and a substance testing module 84, as shown in FIG. 8.

During testing, the substance testing module 84 may convert a user's breath into substance content data. The substance content data may be communicated to a signal generation module 86 which may be operable to convert the substance content data into the content signal 11. The content signal 11 may include, for example, the user's blood alcohol level, or indication that the user's blood alcohol level is below or above a predetermined threshold.

In some embodiments, the content signal 11 may include, for example, an indication that the user's breath contains detectable traces of controlled substances or narcotics or their derivatives, such as, for example: methamphetamines, amphetamines, barbituates, tetrahydrocannabinol (THC) or other cannibanoids, benzoylmethylecgonine, diacetylmorphine or other opiates/opioids, lysergic acid diethylamide, psilocin, phencyclidine and the like. Thus, for example, the receiving station 14 may inform the supervisory monitor 16 if the content signal 11 indicates the user's THC level is greater than 5 ng/ml, the minimum detectable level established by some states. Again, the predetermined threshold may be set at a higher or lower level as may be desired. And, for example, the receiving station 14 may inform the supervisory monitor 16 that the user has a THC level that exceeds the minimum.

The user identification module 82 may be configured to generate a user identification data. For example, the user identification module 82 may be configured to receive a photograph or movie of the user's face from the UID 24 and to convert it into a JPEG image data. Thus, in some embodiments, the user identification module 82 may comprise a compression module (not shown) configured to compresses the user identification data according to a compression process, for example, an implementation variation of standard JPEG compression. In some embodiments, the user identification module 82 and the UID 24 may comprise a single structure. In other embodiments, they may comprise distinct structures.

After the user identification data is generated, it may be communicated to the signal generation module 86 which may be operable to add the user identification data to the content signal 11.

A transceiver 88 may be in communication with the signal generation module 86. The transceiver 88 may be a cell/smart phone, such as iPhone, for example, and can be configured to be connected to the signal generation module 86 either directly, such as by an internal or external electrical connection, or wirelessly, to receive the content signal 11. The transceiver 88 may be configured to transmit the content signal 11 to the receiving station 56, which may comprise a website or monitoring station. The wireless or cellular transmitter or transceiver device 88 may also be configured to transmit the signal over a wireless or cellular network to a wireless or cellular receiving station 14, for example, the cellular phone of a supervisory monitor 16. This transmission may be done periodically, or at specified times.

In at least one embodiment, the content signal comprises at least the substance content data and the user identification data. Alternatively, the user identification data may be transmitted to the receiving station 56 separately from the content signal 11. In at least one embodiment, the content signal 11 comprises a digitized report which may accessible by a supervisory monitor 16.

Ideally the entire test and photography process should take less than 60 seconds, for example, compression of the image data allows a user to offer their breath for testing and have the content signal be received by the receiving station within 60 seconds.

The receiving station 14, for example, a monitoring station, website or server, can preferably automatically evaluate the content signal 11 and maintain a history of the test time, result and the user identification data for each test. The receiving station 14 can also include a database and software for analysis of user identification data, for example, user facial features, for determining whether the user can be identified from each still frame photograph or movie, to confirm or reject the test results, and to determine whether corrective action is required. As explained below, positive identification of the user in association with the content signal 11 may be accomplished by one or more recognition techniques including: facial recognition, voice recognition, DNA recognition, iris recognition, fingerprint recognition, or other recognition techniques now known or developed hereafter.

For example, the receiving station 14 can analyze specific iris or retinal features from one or more eyes of the user for matching with a profile of the user's iris or retinal features, or the receiving station 14 can analyze specific mouth and/or teeth features of the user for matching with a user profile of those features. Additionally, a supervisor may compare the received user identification data with a stored user identification reference in order to positively identify the user.

Facial, iris or retinal identification analysis requires proper alignment and focusing of the camera 24. A device leveling module (not shown) may be provided so as to maintain proper alignment and focus. The device leveling module may operate to detect whether the testing unit remains in an optimal orientation during the testing phase. For example, best image quality generally occurs when the camera remains horizontal and un-rotated during a photo. The device leveling module may indicate to the user, through a GUI, LED, audio or other such user interface, that the device is at a proper orientation for user identification.

Mouth and/or teeth identification analysis may require an appropriate device for proper placement of the substance testing device 20. Multiple internal tooth sensors of a toothguard or mouthpiece (not shown) can be activated by low level electrical signals which can be measured and transmitted by the UID 24, for use in matching a loading profile of the internal tooth sensors with a user's tooth sensor profile.

It will be appreciated that user identification may occur independent of the receiving station 14. For example, the user identification module 82 may comprise a memory that may store a reference user identification data for comparison with the generated user identification data. Upon successful comparison, i.e. the actual user is the intended user, the user identification module 82 may communicate a pass signal which may be added to the content signal 11.

In at least one embodiment, the receiving station is a monitoring station, for example, a monitoring service or a website, that can either manually or automatically alert a supervisory care professional, such as a sober buddy, sober companion or sober coach, that is on-call to respond to an alarm condition or alert, as described herein, in order to take appropriate corrective action. The monitoring station can also preferably provide a variety of reports of the user's testing history or individual test results and still frame photographs or movies used in identification of the user, to allow comprehensive and detailed analysis of the user's testing history, which can be accessed via the Internet as desired. The generated reports may be official Department of Transportation Evidential Breath Testing (EBT) reports, or may be of any other custom or preset format.

It will be appreciated, that while at least one embodiment is herein described through example as testing for alcohol use, such embodiments may be equally applicable to testing for the use of controlled substances or other narcotics, as described herein.

Figure 2:
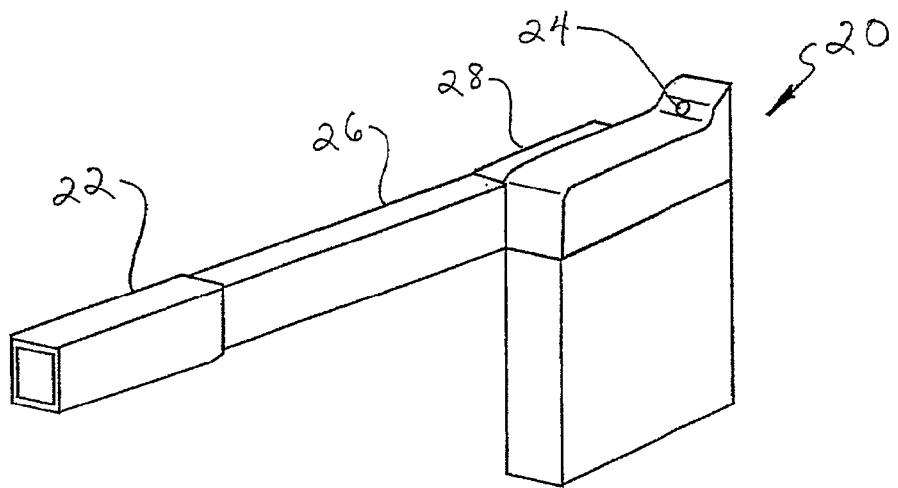
FIG. 2 is a schematic diagram illustrating a breath testing and identification device for use in the method and system of FIG. 1 according to the invention.

At least one preferred embodiment will now be described with reference to FIG. 2.

A breath testing device 20 is provided, which may comprise: a breath tester 22, and a user identification device (UID) 24.

The breath tester 22 may comprise, for example, a breath tester tip 22 configured to be placed at or in a user's mouth during testing. The UID 24 may comprise, for example, a camera 24.

Figure 7:
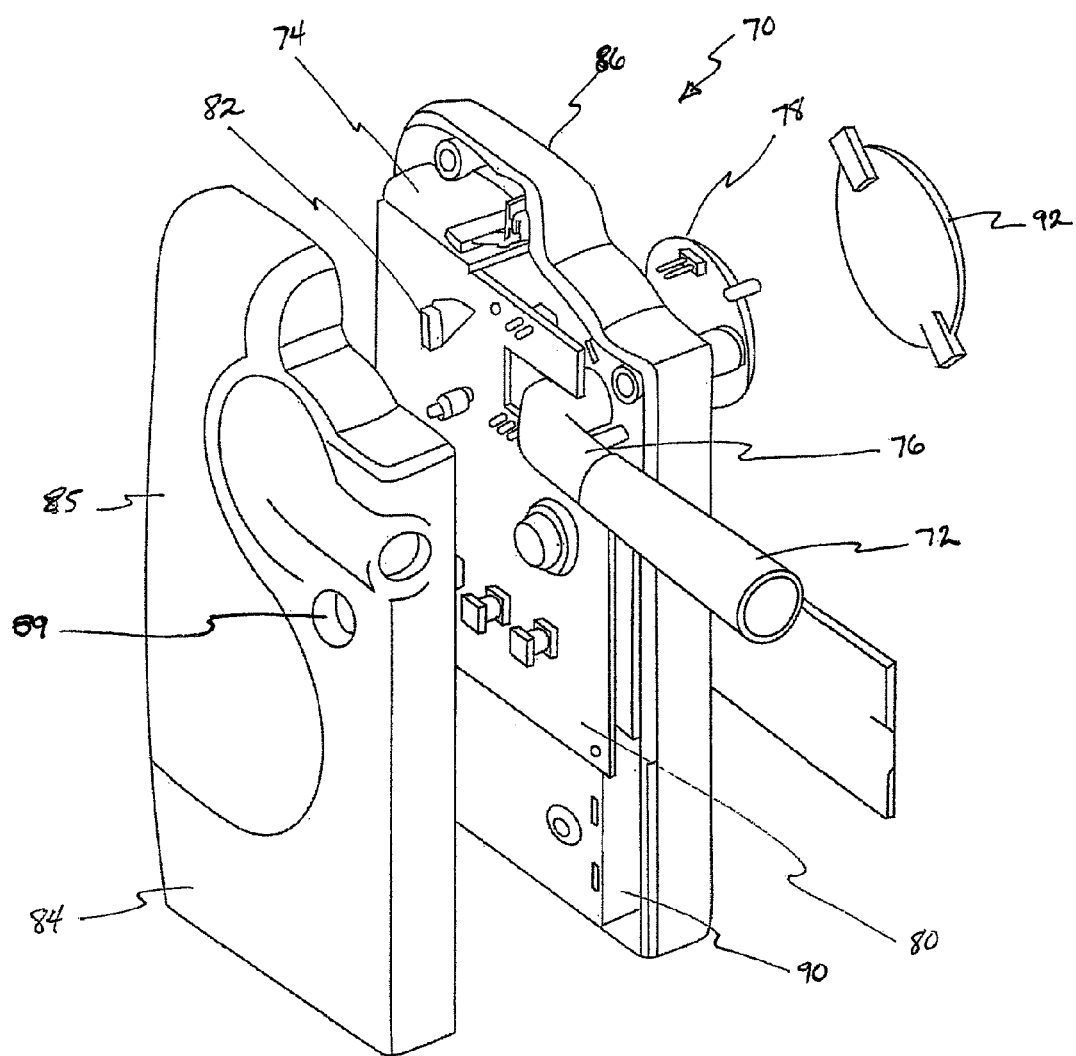
FIG. 7 is an exploded view of the breath testing and identification device according to the invention.

The breath tester tip may be removably mounted to an end of an extension arm 26, which is in turn connected to a breath analysis and processing portion 28 of the breath testing device 20. The breath analysis and processing portion preferably comprises a breath testing module 82, as shown in FIG. 7, and may be operable to convert the substance content data into the substance content signal 11.

The extension arm 26 is preferably a suitable length, such as approximately size to twelve inches, for example, to obtain a still frame photograph or movie suitable for use in accurately identifying the user. Alternatively, the extension arm 26 may be of an adjustable length to allow setting of an optimum length of the extension arm 26.

The breath testing device 20 may also include a handle (not shown) connected to at least one of the camera 24 and the extension arm 26, for ease of use of the device 20.

The physical dimensions of the breath testing device 20 are such that it is readily able to be carried by hand, or inserted into a handbag, purse, pocket or the like. Preferably, the device 20 is not more than 27 cubic inches in volume, and has, for example, a major axis length of approximately 9 inches, a first minor axis length of approximately 3 inches, and a second minor axis length of approximately 1 inch.

The camera 24 may be configured to be directed at the user's face at a suitable distance from the user's face during testing, and may be configured to take a photograph or movie of the user's face in synchronization with the testing, to provide user identification data for later use in positive identification of the user in association with the content signal 11.

Figure 3:
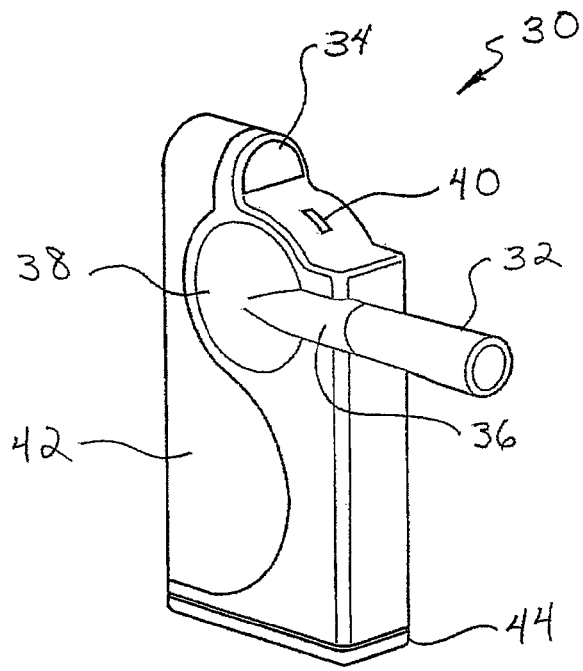
FIG. 3 is a right front perspective illustrating another preferred breath testing and identification device for use in the method and system of FIG. 1 according to the invention.

At least one preferred embodiment will now be described with reference to FIGS. 3 and 4.

As previously described, the breath testing device 30 may include a breathalyzer type device, such as the removable breath tester tip 32 configured to be placed at or in a user's mouth during breath testing, and a camera device 34. The removable breath tester tip 32 is preferably removably mounted to an end of an extension portion 36 which is in turn connected to a breath analysis and processing portion 38 of the breath testing device 30. The camera device 34 may be configured to be directed at the user's face at a suitable distance from the user's face during breath testing, and may be configured to take a photograph or movie of the user's face in synchronization with the testing of the user's breath, to provide identification information for later use in positive identification of the user with the test results.

The breath device 30 may include a status LED 40, such as for indicating when the device is ready for use and when the device has completed breath testing and identification, for example.

The breath testing device 30 may also include an over mold grip portion 42, a battery door 44 for installing and maintaining or recharging batteries (not shown) for powering operation of the device, and optionally a cover 46 for breath sensor (not shown) for powering operation of the device.

The breath testing device 30 may also include an internal GPS tracking module (not shown) or an internal mobile device GPS (not shown) to provide a GPS location and tracking information signal as well.

Figure 6:
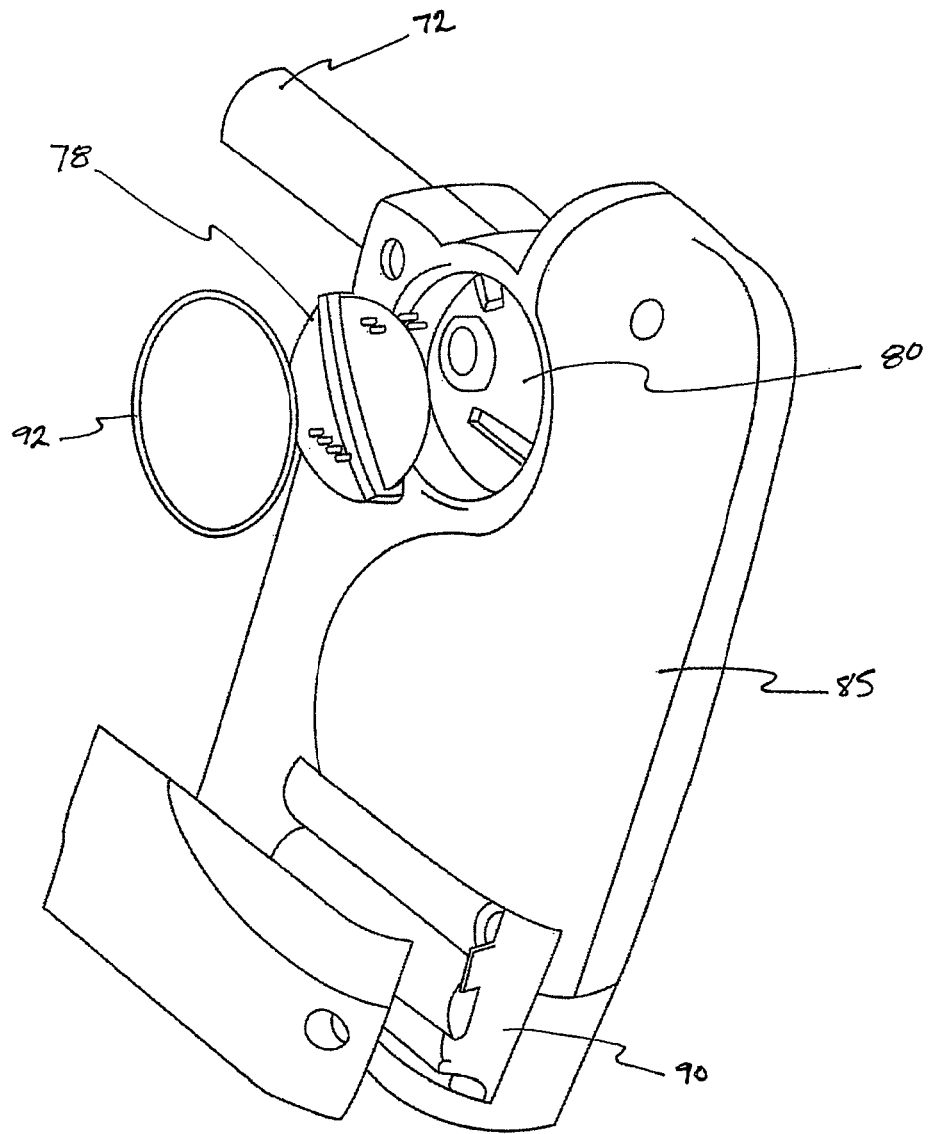
FIG. 6 is an exploded view of the breath testing and identification device according to the invention.

At least one preferred embodiment will now be described with reference to FIGS. 6 and 7.

The breath testing device 70 may comprise: a breath tube 72; a breath interface tube 76; a camera 74; a breath testing sensor 78; and a printed circuit board (PCB) assembly 80.

The breath tube 72 is configured to be placed at or in a user's mouth during breath testing. In some embodiments, the breath tube removably fixed to the breath interface tube 76 and is disposable.

The breath interface tube 76 is in communication with the breath testing sensor 78, which may be, for example, a semiconductor or a fuel cell breath analyzer. The breath testing sensor 78 is configured to receive the user's breath and calculate substance content data, which may be, for example, a blood alcohol level, and to transmit the substance content data to the PCB assembly 80.

In some embodiments, the breath testing sensor 78 comprises a sensor capable of detecting the presence of at least one controlled substance or narcotic. The sensor 78 may utilize, for example, a chromatography sensors, mass spectroscopy sensors, fiber optic fluorescent sensors, or surface acoustic wave sensors to detect the presence of controlled substances or narcotics and their derivatives, such as, for example: methamphetamines, amphetamines, barbituates, tetrahydrocannabinol or other cannibanoids, benzoylmethylecgonine, diacetylmorphine or other opiates/opioids, lysergic acid diethylamide, psilocin, phencyclidine and the like, in a user's breath.

The PCB assembly 80 is configured to receive the substance content data and generate a breath test signal 11 therefrom. The PCB assembly 80 is also configured to receive user identification data generated by the camera 74 and to generate the breath test signal from the compressed user identification data and the substance content data. In one embodiment, the PCB is configured to operate a compression process, such as JPEG compression, for example, to compress the user identification data.

A front case 84 and a rear case 86 operate to form a protective housing for the breath testing device 70, and a grip portion 85 provides a textured surface to increase friction and user grip capability. The rear case 86 has a removable sensor cover 92 that is detachable from the rear case 86 to expose the breath testing sensor 78 and permit changing of the breath testing sensor (e.g., in the case of a replaceable fuel cell) 78. A power button 89 is in electrical communication with the PCB assembly 80 and extends beyond the front case 84 so as to be readily accessible to a user. The power button is operable to switch the breath testing device 70 between an on-state and an off-state. A battery compartment 90 operates to house batteries (not shown) that are the electrical power source for the breath testing device. Preferably, the breath testing device will require two AA batteries as an electrical power source.

A status indicator light 82, such as an LED, for example is provided in electrical communication with the PCB assembly 80, which indicates a status of the breath testing device. The status indicator light 82 may, for example, indicate that a breath test and/or user identification is occurring, or that a generated breath test signal indicates a substance content greater than a predetermined threshold, or that a generated content signal 11 indicates a user identification data does not match with a reference user identification data, or that transmission of the generated content signal 11 is occurring, has been successful, or has failed, or that the batteries are running low on power. Corresponding audio signals, such as various types of beeps may be employed as well.

Additionally, a device leveling module (not shown) may be provided. The device leveling module preferably comprises at least one accelerometer in connection with the PBC 80. The device leveling module may operate to detect whether the testing device remains in an optimal orientation during the testing phase. For example, best image quality generally occurs when the camera remains horizontal and un-rotated during a photo. The device leveling module may indicate to the user, through a GUI, LED, sound or other such interface, that the device is at a proper orientation for identity verification.

As is illustrated in FIG. 5, the breath testing device 50 may be connected to a mobile wireless or cellular transmitter or transceiver device 52, which may be connected to the breath testing device 50 either directly, such as by an electrical connection, or wirelessly, to receive the breath test signal 11 comprising breath test data and photograph, movie, or other user identification data, as well as any GPS location data 54.

In some embodiments, the breath testing device can also be usable in combination with an iPod, iPhone, or other wireless or cellular device such as a BlackBerry, or any other computing device, for example, which can serve as a wireless or cellular transmitter or transceiver device 52, as discussed herein. The wireless or cellular transmitter or transceiver device 52 is preferably configured to be connected to the breath testing device 50 either directly, such as by an electrical connection, or wirelessly, such as via a Bluetooth connection, for example, to receive the breath test signal 11 and user identification data from the breath device.

In some embodiments, the wireless or cellular transmitter or transceiver device may also configured to transmit the breath test signal 11 for each testing session over a wireless or cellular network to a wireless or cellular receiver monitoring station 56 configured to receive the breath test signal 11, and to indicate an alarm condition or alert the supervisory monitor if a breath test signal is not received from the wireless or cellular transceiver device within a desired timeframe or schedule, indicating that the wireless or cellular transmitter or transceiver device is off, or if the content signal is greater than a predetermined threshold, as discussed above.

Figure 11:
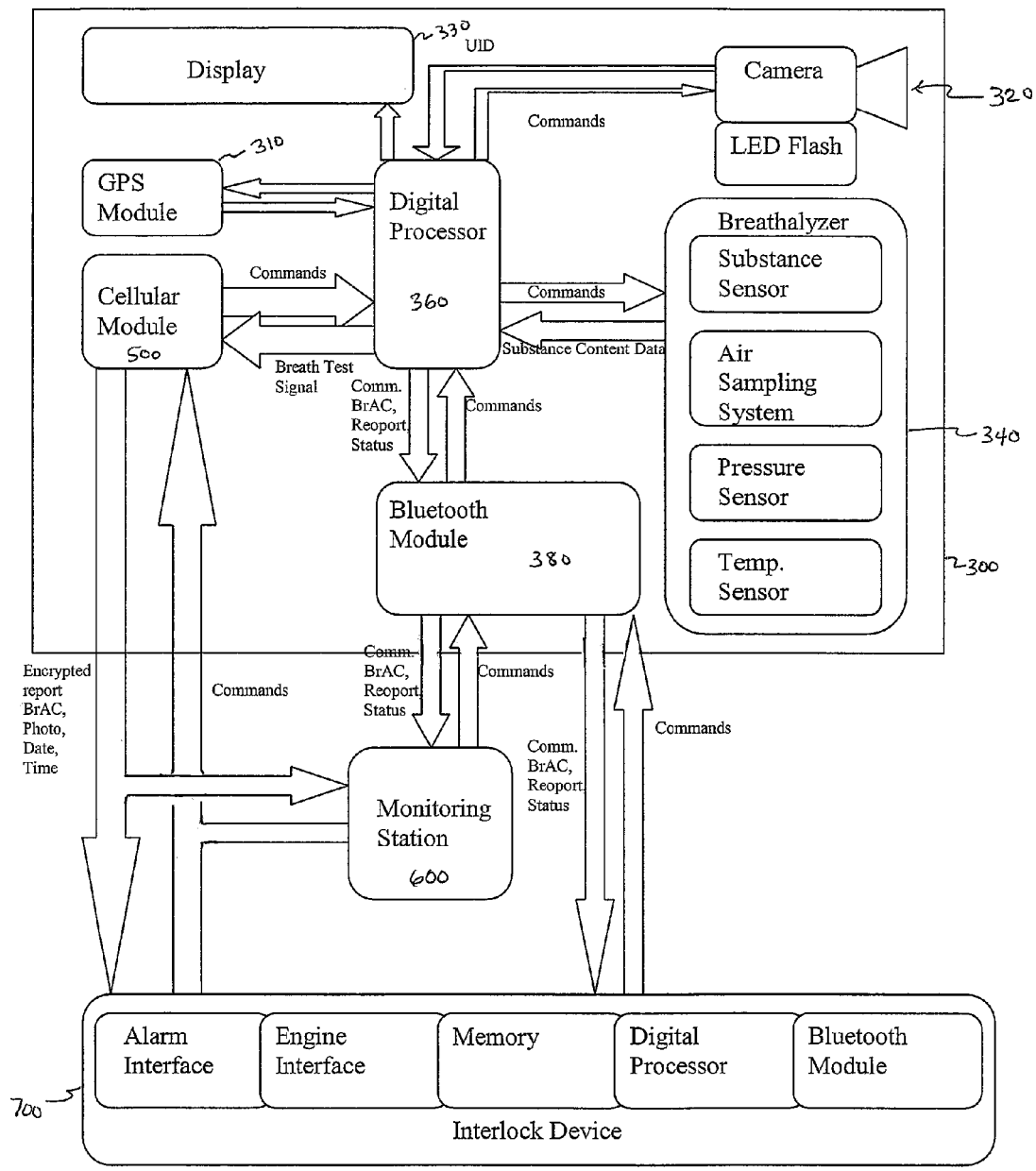
FIG. 11 is a schematic diagram illustrating another the method and system for monitoring sobriety, according to a preferred embodiment of the invention.

A GPS device 310, shown in FIG. 11, may generate a location data that is preferably incorporated into the content signal 11 and transmitted therewith. The wireless or cellular transmitter or transceiver device 52 can in turn transmit the content signal, comprising at least one of: the content signal, the content data, user identification data, and location data, over a wireless or cellular network to a wireless or cellular receiving station 56, where they may be stored, for example, as in a database at a monitoring station or in a text or e-mail message. Thus, the location of the user when the test is submitted may be identified and logged.

Alternatively, the content signal 11 comprising at least one of: content data, user identification data, and location data, can be sent directly from one mobile wireless or cellular transmitter or transceiver device to another mobile wireless or cellular transmitter or transceiver device 58, without storing one or more of the content data, user identification data, or location data.

The wireless or cellular receiver monitoring station 56 can be configured to receive the content signal comprising at least one of: content data, user identification data, and location data, and to indicate an alarm condition or alert a supervisory monitor 60 either directly or via a network 62. A cellular module can alternatively be provided inside the breath testing device 50 to transmit the breath test signal 11 directly through WiFi, cell towers, Multimedia Messaging Service (MMS), or through a network 62 such as the Internet, or a mobile wireless network, such as those that do not rely on fixed infrastructure, for example. Transmission may be directly to the supervisory monitor 60 or indirectly through the receiving station 14. Thus, in some embodiments, the receiving station comprises the supervisory monitor.

Figure 9:
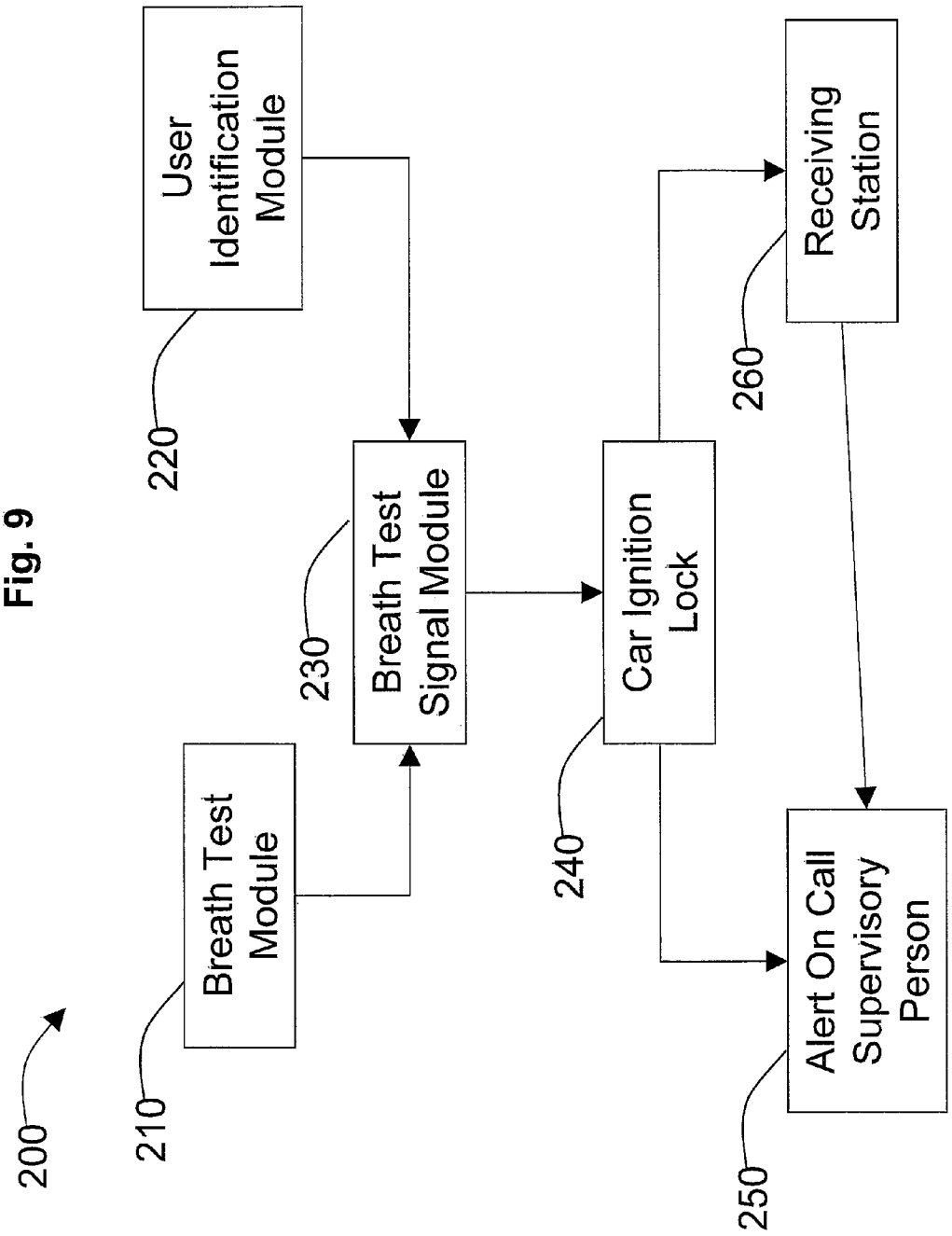
FIG. 9 is a schematic diagram illustrating a vehicle interlock device according to a preferred embodiment of the invention.

Turning now to FIG. 9, in some embodiments, a mobile breath-testing module 210 and user identification device 220 may also be included in a vehicle ignition interlock signal generating system 200. The output of the breath test module 210 and the user identification module 220 may be provided to a breath test signal module 230, which then may provide a signal to enable/disable a car ignition lock 240 based on the data received in accordance with the algorithms described above. The enable/disable signal may be provided to the car ignition lock 240 either wirelessly, e.g., via Bluetooth connection, or a wired connection. In addition, an on-call supervisory person 250 may be alerted, and a receiving station 260, which may be a website and/or monitoring station may also receive the enable/disable signal as well as the content signal 11 described above.

Figure 10:
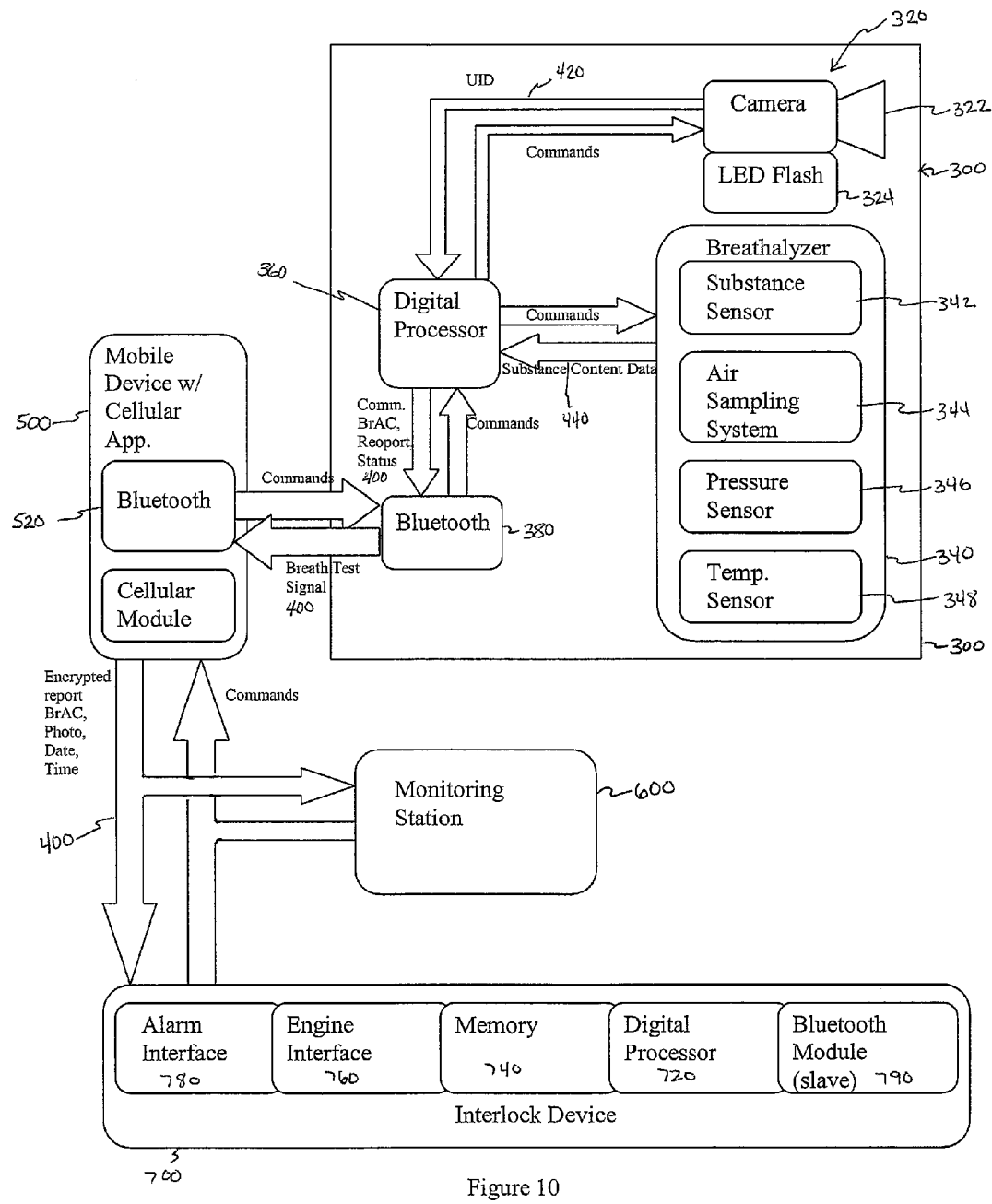
FIG. 10 is a schematic diagram illustrating another the method and system for monitoring sobriety, according to a preferred embodiment of the invention.

A preferred embodiment will now be described with reference to FIG. 10.

A hand-held breath testing unit 300 comprises a user identification module 320, a breath analysis module 340, a control module (CPU) 360, and a first personal area network (PAN) module 380.

The breath analysis module 340 receives the breath of a user and generates a substance content data 440 therefrom that is sent to the CPU 360. The substance content data indicates the presence of various substances in the breath of a user. For example, the substance content data may indicate the presence of a substance above a certain predefined threshold or it may indicate a percentage or other identifier. While the substance data preferably indicates alcohol content, the substance data may also indicate the presence of narcotics, radiation, viral or bacterial infection, cancer or any other chemical or biological substance.

The breath analysis module 340 may comprise a substance sensor 342, an air sampling system 344, a pressure sensor 346, and a temperature sensor 348.

The air sampling system may be a NHTSA approved PAS Systems air sampling system. In any case, the air sampling system is operable to take a consistent and repeatable breath sample after a volume of air has passed through. The air sampling system enables the breath analysis module to measure the substance content of deep lung air by enabling fine measurement of the volume of air in the blow before a sample is taken. The pressure sensor detects the prescribed minimum pressure of a blow and enables the air sampling system to sample the breath after a set time at or after a prescribed pressure is reached, enabling deep lung air to be sampled by the substance sensor. This prescribed pressure may be settable and is preferably set at a minimum volume of approximately 0.6 L. Additionally, the pressure sensor and air sampling system may provide a running estimate of total air volume blown and the air may be sampled after a prescribed minimum volume has been reached. This prescribed volume is preferably set at approximately 1.2 L. This minimum volume may be altered to fit to an individual user's lung capacity.

The substance sensor 342 may be a precision fuel-cell alcohol sensor that converts alcohol in a user's breath to an electrical signal that is measured and used to compute the amount of alcohol in the user's blood. Alternatively, the substance sensor may be a semiconductor alcohol sensor. The substance sensor analyzes the breath of a user and generates the substance content data therefrom. The substance content data is then transferred to CPU. Calibration of the fuel cell sensor may be performed using either a wet or dry bath simulator with a calibrated solvent accurate to within +/−3% of the stated value. In some embodiments, a calibration point may be a BrAC level of 0.02.

The substance sensor 342 may also be a chromatography/mass spectroscopy sensor that converts narcotics, such as methamphetamines, present in the user's breath into an electrical signal that is measured and used to compute the amount of narcotic in the user's blood. Alternatively, the substance sensor 342 may be a fiber optic fluorescent sensor, or surface acoustic wave sensor. These sensors may be calibrated to detect the presence of controlled substances or narcotics and their derivatives or metabolites, such as: methamphetamines, amphetamines, barbituates, tetrahydrocannabinol or other cannibanoids, benzoylmethylecgonine, diacetylmorphine or other opiates/opioids, lysergic acid diethylamide, psilocin, phencyclidine and the like, in a user's breath. The substance sensor analyzes the breath of a user and generates the substance content data therefrom. The substance content data is then transferred to CPU.

In some embodiments the sensor 342 may comprise a mass spectroscopy sensor, such as described in US2007/0062255; US2005/0065446; Berchtold, et al., International Journal of Mass Spectrometry 299 (2011) 145-150; and Karolinska Institutet (2010, May 19), New technique enables drugs tests via exhaled breath, ScienceDaily, Retrieved Dec. 19, 2011, from http://www.sciencedaily.com/releases/2010/05/100519081438.htm, the contents and disclosures of which are herein incorporated by reference.

Figure 12:
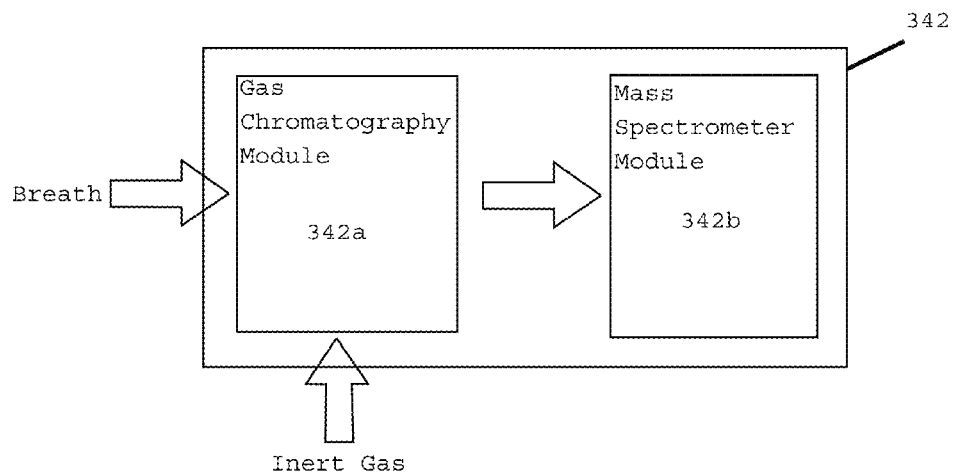
FIG. 12 is a schematic diagram illustrating another the method and system for monitoring sobriety, according to a preferred embodiment of the invention.

As shown in FIG. 12 the sensor 342 may comprise a gas chromatography module 342a and a mass spectrometer module 342b. The user's breath may pass from the air sampling system 344 to the gas chromatography module 342a. The air sampling system may be operable to take a consistent and repeatable breath sample after a volume of air has passed through. The gas chromatography module may retain the molecules present in the user's breath and may release the molecules according to each molecule's retention time. The molecules may travel to the mass spectrometer module 342b. In some embodiments, the gas chromatography module 342a may comprise an inert gas injector (not shown) which may cause the released molecules to be transferred to the mass spectrometer 342b at a substantially uniform rate. The mass spectrometer module 342b may ionize the released molecules and break them into fragments that are detected according to their mass-to-charge ratio. This detection may comprise converting the molecules into an electrical charge. The detected mass-to-charge ratios may then be compared against those of substance molecules according to their known retention times. Thus, the presence of certain narcotics in the user's breath may be detected. Preferably, the sensor 342 may be adjustable to detect a particular narcotic or group of narcotics by limiting analysis to those molecules whose retention times match the substance(s) selected for testing.

Returning to FIG. 10, the user identification module 320 identifies the user of the breath testing unit. Identification may be by biometrics, photograph, video, or any other user identifying module now known or hereafter discovered. The user identification module operates to generate user identification data 420 for verifying the user of the breath testing unit. The user identification module may comprise a camera 322 equipped with an LED light 324 that provides a flash for the camera. The user identification data 420 may be a jpeg photograph. Immediately after the air sample is taken, the camera takes a picture of the user to signal the end of the breath testing session.

The CPU 360 controls the functionality of the component parts of the breath testing unit and stores computer readable instructions thereon whose execution enables the breath testing unit to function. The CPU receives the user identification data and substance content data from the user identification 320 and breath analysis 340 modules, respectively, and generates the breath test signal 400 therefrom.

The first PAN module 380 is in electrical communication with the CPU 360 and receives the breath test signal 400 therefrom. The first PAN 380 module may be a Bluetooth module with an embedded transceiver operable to wirelessly transmit the breath test signal.

An intermediary device 500 such as a smart cellular phone, PDA, tablet, laptop, or other mobile or personal computing device having internet, wireless and/or PAN capabilities, is in communication with the testing unit. The intermediary device may comprise a second PAN module 520 creating a wireless PAN communication between the second PAN module of the intermediary device and the first PAN module of the breath testing unit. In some embodiments, the first PAN module may be a slave and the second PAN module a master. In other embodiments, the first PAN module may be a master and the second PAN module a slave.

Communication between the first and second PANs may be secured by data encryption techniques now known or hereafter devised. For example, data may be encrypted by means of a random security PIN.

The intermediary device 500 preferably receives the breath test signal 400 from the breath testing unit, via communication between the first and second PAN modules, and wirelessly transmits the breath test signal to a monitoring station 600. Transmission to the monitoring station 600 may be accomplished either directly through WiFi, cell towers, or though a network such as the Internet, or a mobile wireless network.

The intermediary device 500 preferably comprises a general purpose smart phone equipped with a software application enabling the intermediary device to receive and transmit the breath testing signal. But, the intermediary device may also comprise a similarly equipped PDA, tablet, laptop or other mobile or personal computing device. The software application may cause the intermediary device to display a reminder at a predetermined time, the reminder reminding the user that a breath testing session is due. Additionally, the software application may cause users to receive electronic reminders via SMS, email, or bi-directional communication with the breath testing unit. Additionally, the software application may enable the intermediary device to receive breath test requests from the monitoring station. Such requests may be remotely or directly transmitted to the intermediary device.

In some embodiments, the software application enables the intermediary device to function as a identity verification module. For example, the software application may enable the intermediary device to take a rental or thumb print scan of the user as part of the user identification process. In some embodiments, this identity verification comprises photographic verification and may replace or supplement the user identification module 320. The software application may further enable the intermediary device to receive the breath test signal and to generate a modified breath test signal 400 therefrom, transmitting the modified breath test signal to the monitoring station 600. The modified breath test signal may be an encrypted signal. The modified breath test signal may also comprise identity verification data and/or a time/date stamp data indicating at least one of a time and date that the breath test data was transmitted to the monitoring station. Additionally, the functioning of the software application may be transparent to a user.

In at least one embodiment, the identity verification data may be transmitted to the monitoring station where it may be compared to a master ID. For example, the identity verification data may be a photograph and the master ID may be a previously taken photograph. The monitoring station may use facial recognition to compare the photograph with the master photograph. Alternatively, the intermediary device may store the master ID and may operate to compare the identity verification data with the master ID. If the identity verification data does not match the master ID, the modified breath test signal may comprise a "failed" state and the monitoring station may be notified.

In some embodiments, one or more of the breath testing unit, intermediary device, receiving station, and supervisory monitor identifies, for example, 'dirty' reports, missed testing sessions, failed user identification, or other mishaps in testing which may be attributable to human error and causes the intermediary device to display an alert to the user to re-test.

In some embodiments, the software application causes the intermediary device 500 to undergo an authentication process. During the authentication process, the intermediary device may be paired to the breath testing unit 300 and/or to the monitoring station 600. The application software may require that a PAN authentication key, for example the serial number of an associated breath testing unit or interlock device, be entered into the intermediary device so as to associate the intermediary device with the breath testing unit and/or the monitoring station and permit operation therewith.

Communication between the intermediary device and the monitoring station may be secured by data encryption techniques now known or hereafter devised. For example, data may be encrypted by means of a random security PIN. Devices that are compromised may be forced from the monitoring station server and may require re-activation and authentication. Additionally, reactivation and authentication may be required to re-link intermediary devices with breath testing units where the security of communication therebetween may be compromised.

After the intermediary device 500 is paired with the breath testing unit 300, a device status signal including battery level is sent to the intermediary device. When the intermediary device receives the status signal indicating a successful authentication, it may display a prompting screen, prompting the user to blow into the breath testing unit. Additionally, the breath testing unit may also prompt the user to blow by flashing the power LED. In some embodiments, prompting may occur at a predetermined time that is not directly after authentication but at a predetermined time stored in a memory of the intermediary device and accessible by the application software. In such an embodiment, the intermediary device and the breath testing device and/or monitoring station may remain in remote connection until a breath test is prompted and even after one has been completed to enable periodic breath testing.

Once the air sample has been captured and the picture taken, the software application enables the intermediary device 500 to receive a test completion signal from the breath testing unit and to display a compiling report screen. The application software enables the intermediary device to receive the breath test signal generated by the breath testing unit. If the breath testing signal indicates an error in the test, then the application software causes the intermediary device to display the errors. Once the breath test data is completely received by the intermediary device, the software application causes the intermediary device to display a compiling report screen. The software application then causes the intermediary device to compile the modified breath test signal based on the breath test signal. The modified breath test signal may then be sent to the monitoring station 600. Additionally, the software application causes the intermediary device to transmit an end process signal to the breath testing unit.

In some embodiments, the software application may cause the intermediary device to generate a report that is displayed on the intermediary device or may be sent to the monitoring station 600. The report may contain substance content and user identification data formatted so as to be viewable by a user.

Additionally, the intermediary device may comprise a memory (not shown) and the report may be communicated to the memory and stored. This may occur automatically, for example, if the connectivity to the monitoring station is compromised, or the ability of the intermediary device to transmit the report is otherwise impaired.

Figure 13:
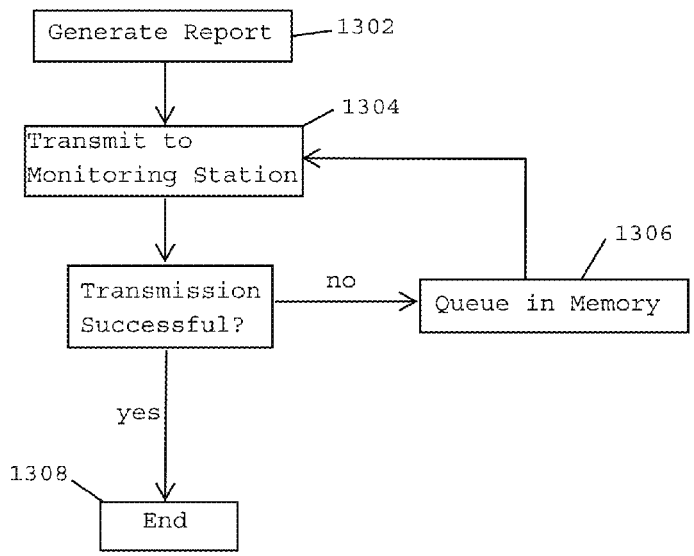
FIG. 13 is a schematic diagram illustrating another the method and system for monitoring sobriety, according to a preferred embodiment of the invention.

As illustrated in FIG. 13, when multiple reports are generated during such a period, the memory may store the reports in a queue. After a report is generated (step 1302), the intermediary device attempts to transmit it to the monitoring station (step 1304). On the indication of a failed transmission due to, for example, the connectivity to the monitoring station being compromised, or the ability of the intermediary device to transmit the report being otherwise impaired, the report is communicated to the memory and queued therein (step 1306). After a predetermined period of time has passed, the intermediary device attempts to transmit the queued report(s) to the monitoring station (step 1306). Thus, once connectivity is reestablished, the reports may be transmitted to the monitoring station in the order that they were generated (step 1308).

In at least one embodiment, each time one device is waiting for another to send a message, a timer is run and if the message does not arrive within a preset time, the test will be cancelled and the breath testing unit will shut down.

Returning now to FIG. 10, the monitoring station 600 may be in wireless communication with the intermediary device 500 and may receive the breath test signal and/or the breath test report 400. In some embodiments, the monitoring station 600 receives the breath test signal and generates the breath test report. Preferably, the monitoring station comprise at least one of: a website, a cellular phone, an email account inbox, or a vehicle interlock device 700. In at least one embodiment, the monitoring station may enable the breath test signal and/or the breath test report to be accessible by a probation officer, a sobriety coach, or a family member. In some embodiments, this may comprise an email, phone call, website notification, text message or MSM alert indicating failure of the breath test by the user or indicating that a review of user activity is required. In some embodiments this may comprise storing the breath test signal or report in a memory to be accessed at a later time. This report storing may be in the form of a queue. In some embodiments, the software application enables the intermediary device to, on selection by the user, to selectively transmit the breath test signal and/or report to one or more of the monitoring stations.

In at least one preferred embodiment, the monitoring station 600 comprises a vehicle interlock 700 having a digital processor 720, a non-volatile memory 740, an engine interface 760, an alarm interface 780, and a PAN module 790 coupled to the intermediary device 500. As described above, the intermediary device may transmit the breath test signal to the vehicle interlock device via the PAN network, or any other means of communication now known or hereafter developed. On receipt of a breath test signal having a substance content data exceeding certain threshold, the digital processor 720 may cause the engine interface to disable the associated vehicle engine. The digital processor 720 may also cause the breath test signal and/or report to be stored within the non-volatile memory 740, accessible by authorized persons, for example police officers, probation officers, court officials, family members and sobriety coaches. In some embodiments, the vehicle interlock 700 may function as an additional intermediary device and transmit the breath test signal to other monitoring stations by similar means as those described above with reference to the intermediary device.

In at least one preferred embodiment, the monitoring station 600 comprises the mobile device of a parent, guardian, family member or sober coach. In such an embodiment, the mobile device of the family member or sober coach comprises an auxiliary software application. The auxiliary software application may enable functionality similar to the intermediary device, in part or in whole, such functionality described above. In this manner, on the spot breath testing may be conducted without the need to locate the user's mobile Additionally, the auxiliary software may enable the monitoring station to transmit a breath test request signal to the intermediary device, as described above. For example, a parent of a teenage user may send the request to the cell phone of the teenage user and request a breath test to be completed by a designated time. On receipt of the request, the cell phone of the teenage user would notify the teenage user that a breath test is due before the designated time. The breath test signal and/or report would then be sent to the parent cell phone. In some embodiments, the auxiliary software enables the monitoring station to transmit the breath test signal and/or other control commands to other monitoring stations. For example, on receipt of a breath test signal having an undesired substance content data, the parent may, from his cell phone, send the breath test signal or other control signal to the interlock device, thereby shutting down the teenager's use of the vehicle.

Referring now to FIG. 11, the breath testing unit 300 may comprise an internal cell module 500 in exchange for the intermediary device, the breath testing unit here being a stand-alone unit. Those of skill in the art will appreciate that the features associated with the afore described intermediary device are equally applicable to embodiments utilizing the internal cell module.

The breath testing unit may comprise, the user identification module 320, the breath analysis module 340, the control module (CPU) 360, the cellular module 500 and a GPS module 310.

The cellular module 500 may comprise a transceiver operable to transmit the breath test data to the monitoring station 600. The GPS module 310 may enable the tracking of the breath testing unit by the generation of location data. The breath test signal may be generated, at least in part, by the location data.

The breath testing unit 300 may also comprise a PAN module 380, enabling the breath testing unit to be in PAN communication with the monitoring station 600, for example the vehicle interlock 700.

Communication between the PAN and the monitoring station may be secured by data encryption techniques now known or hereafter devised. For example, data may be encrypted by means of a random security PIN. Devices that are compromised may be forced from the monitoring station server and may require re-activation and authentication.

The breath testing unit may also comprise a graphical user interface 330 (GUI). The GUI may permit the user to interactively control the breath testing process, calibrate the breath testing unit, schedule breath test times, retrieve past breath test reports, and/or access other information stored in the breath testing unit.

The GUI may be configured to display a reminder at a predetermined time, the reminder reminding the user that a breath testing session is due. Additionally, the breath testing unit may cause users to receive electronic reminders via SMS, email, or bi-directional communication between the breath testing unit and receiving station. Additionally, the breath testing unit may enable the user to receive breath test requests from the monitoring station. Such requests may be remotely or directly transmitted to the breath testing unit.

The embodiments described in detail above are considered novel over the prior art of record and are considered critical to the operation of at least one aspect of the apparatus and its method of use and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that each named inventor believes that the claimed subject matter is what is intended to be patented.

What is claimed is:

1. A system for remotely monitoring the sobriety of a first user, the system comprising:
    a handheld breath testing device operable to receive a user's breath and determine whether alcohol is present within the first user, said handheld breath testing device including:
        a portable, cordless hand-held case having an inside, an outside, and one or more walls,
        a breath alcohol content sensor housed within the case for sensing a breath alcohol content of the first user,
        a digital camera housed within the case,
        a wireless transceiver housed within the case, and
        a controller housed within the case and electronically coupled to the digital camera, the sensor, and the wireless transceiver; and
    a server communicatively coupled to the handheld breath testing device, the server including a database;
    wherein the controller includes a processor and a non-transitory computer-readable medium containing a sequence of instructions that, when executed by the processor, causes the processor to execute the following operations:
        capture user identification data with the digital camera during a breath test, the user identification data identifying the first user,
        capture the breath alcohol content of the first user with the breath alcohol content sensor during the breath test, and
        transmit the user identification data and the breath alcohol content to the server using the wireless transceiver; and
    wherein the server further includes a processor and a non-transitory computer-readable medium containing a sequence of instructions that, when executed by the processor, causes the processor to execute the following operations:
        receive a schedule from a second user;
        receive the user identification data and the breath alcohol content;
        store within the database data indicating whether the user identification data and the blood alcohol content were captured in accordance with the schedule.

2. The system of claim 1, wherein the controller of the handheld breath testing device receives the schedule from the server and initiates a breath test based on the schedule.

3. The system of claim 1, further comprising:
    a personal mobile device communicatively coupled to the server;
    wherein the personal mobile device receives the schedule from the server.

4. The system of claim 1, wherein the server is configured to generate an alert signal if said user identification data and breath alcohol content from the first user is not captured in accordance with the schedule generated by the second user.

5. The system of claim 4, wherein the server is further configured to transmit the alert signal to the second user.

6. The system of claim 1, wherein the server comprises a display configured to display one or more breath test reports based on the user identification data, the breath alcohol content data, and the schedule.

7. The system of claim 6, wherein the server is further configured to store a history of breath test reports.

8. The system of claim 1, wherein the breath testing device further comprises a memory, electronically coupled to the controller; wherein the memory is configured to store the user identification data and the breath alcohol content prior to transmitting the user identification data and the breath alcohol content to the server.

\* \* \* \* \*